United States Patent
Ghamdi-Al et al.

(10) Patent No.: US 11,358,925 B2
(45) Date of Patent: Jun. 14, 2022

(54) RECOVERY OF PROPYLENE FROM REACTOR PURGE GAS

(71) Applicant: SABIC GLOBAL TECHNOLOGIES B.V., Bergen op Zoom (NL)

(72) Inventors: Ameen S. Ghamdi-Al, Riyadh (SA); Jagan Mohan Rallapalli, Riyadh (SA); Paul Somak, Riyadh (SA)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 17/263,448

(22) PCT Filed: Jul. 26, 2019

(86) PCT No.: PCT/IB2019/056417
§ 371 (c)(1),
(2) Date: Jan. 26, 2021

(87) PCT Pub. No.: WO2020/021515
PCT Pub. Date: Jan. 30, 2020

(65) Prior Publication Data
US 2021/0188752 A1 Jun. 24, 2021

Related U.S. Application Data

(60) Provisional application No. 62/711,165, filed on Jul. 27, 2018.

(51) Int. Cl.
*C07C 45/50* (2006.01)
*C07C 7/00* (2006.01)
*B01J 23/00* (2006.01)
*B01J 31/00* (2006.01)
*B01J 23/46* (2006.01)
*B01J 31/02* (2006.01)
*C07C 11/06* (2006.01)

(52) U.S. Cl.
CPC .............. *C07C 45/50* (2013.01); *B01J 23/464* (2013.01); *B01J 31/0267* (2013.01); *C07C 7/005* (2013.01); *C07C 11/06* (2013.01)

(58) Field of Classification Search
CPC ........ C07C 45/50; C07C 7/005; B01J 23/464; B01J 31/067
See application file for complete search history.

(56) References Cited

U.S. PATENT DOCUMENTS

| | | |
|---|---|---|
| 4,210,426 A | 7/1980 | Sridhar |
| 5,367,106 A | 11/1994 | Unruh et al. |
| 5,463,137 A | 10/1995 | Ramachandran et al. |

FOREIGN PATENT DOCUMENTS

CA 2130387 3/1995

OTHER PUBLICATIONS

International Search Report and Written Opinion issued in International Patent Application No. PCT/IB2019/056417, dated Nov. 25, 2019.

*Primary Examiner* — Sikarl A Witherspoon
(74) *Attorney, Agent, or Firm* — Norton Rose Fulbright US LLP

(57) ABSTRACT

A process of recovering propylene and N-butyraldehyde from a purge gas includes forming a first product stream including N-butyraldehyde by reacting propylene and a first synthesis gas in the presence of a first catalyst in a first reactor and a second reactor; withdrawing a mixed stream from the second reactor; separating a liquid stream and purge gas from the mixed stream and recycling the liquid stream to the second reactor; reacting the purge gas and a second synthesis gas in the presence of a second catalyst in a purge gas reactor to form a second product stream including N-butyraldehyde; withdrawing the second product stream including N-butyraldehyde from the purge gas reactor and combining the second product stream including N-butyraldehyde and the first product stream including N-butyraldehyde; and withdrawing a stream including N-butyraldehyde from the purge gas reactor and recovering N-butyraldehyde from the stream including N-butyraldehyde product stream.

20 Claims, 2 Drawing Sheets

RECOVERY OF PROPYLENE FROM REACTOR PURGE GAS

CROSS-REFERENCE TO RELATED APPLICATIONS

This application is a national phase under 35 U.S.C. § 371 of International Application No. PCT/IB2019/056417, filed Jul. 26, 2019, which claims the benefit of priority to U.S. Provisional Patent Application Ser. No. 62/711,165, filed Jul. 27, 2018, the entire contents of each of which are hereby incorporated by reference in their entirety.

BACKGROUND

This disclosure relates to methods for the recovery of propylene from the purge gas of a reactor, for example a purge gas generated in a process for the manufacture of n-butyraldehyde.

N-butyraldehyde (NBAL) can be produced from propylene according to the OXO process. In the OXO process, hydroformylation of olefins with synthesis gas is carried out to manufacture NBAL, with a by-product of Iso-butyraldehyde (IBAL) also being formed.

The catalyst used under the OXO process is rhodium acetylacetonato carbonyl triphenylphosphine [Rh(acac)(CO)PPh$_3$ or ROPAC]. Hydroformylation conditions are such that aldehydes such as NBAL are present in a liquid product of the process.

U.S. Pat. No. 5,463,137 discloses contacting a propylene stream which contains propane as an impurity with carbon monoxide and hydrogen in the presence of a hydroformylation catalyst thereby producing a product stream containing butyraldehyde and/or n-butyl alcohol, unreacted propylene and propane. A gas mixture containing propylene and propane is separated from the product stream and subjected to adsorption at a temperature of 0° to 250° C. in a bed of adsorbent which selectively adsorbs propylene, allegedly thereby adsorbing substantially all of the propylene from the gas mixture. The propylene is desorbed from the adsorbent and recycled to the reaction zone. The process is operated on a low per pass conversion with recycle of unreacted propylene. The propylene adsorption unit may be upstream or downstream of the hydroformylation reactor.

It would be desirable to improve conversion of propylene to NBAL in an OXO process.

SUMMARY

Disclosed, in various embodiments, are processes of recovering propylene and N-butyraldehyde from a purge gas.

A process of recovering propylene and N-butyraldehyde from a purge gas includes forming a first product stream including N-butyraldehyde by reacting propylene and a first synthesis gas in the presence of a first catalyst in a first reactor and a second reactor; withdrawing a mixed stream including N-butyraldehyde and unreacted propylene from the second reactor; separating a liquid stream and purge gas including N-butyraldehyde and unreacted propylene from the mixed stream and recycling the liquid stream to the second reactor; reacting the purge gas and a second synthesis gas in the presence of a second catalyst in a purge gas reactor to form a second product stream including N-butyraldehyde; withdrawing the second product stream including N-butyraldehyde from the purge gas reactor and combining the second product stream including N-butyraldehyde and the first product stream including N-butyraldehyde; and withdrawing a stream including N-butyraldehyde from the purge gas reactor and recovering N-butyraldehyde from the stream including N-butyraldehyde product stream using a vent condenser.

A process of recovering propylene and N-butyraldehyde from a purge gas includes forming a first product stream including N-butyraldehyde by reacting propylene and a first synthesis gas in the presence of a first catalyst including rhodium in a first reactor; withdrawing a mixed stream including N-butyraldehyde and unreacted propylene from the first reactor; separating a liquid stream and purge gas including N-butyraldehyde and unreacted propylene from the mixed stream using an entrainment separator and recycling the liquid stream to the first reactor; reacting the purge gas and a second synthesis gas in the presence of a second catalyst including rhodium in a purge gas reactor to form a second product stream including N-butyraldehyde; withdrawing the second product stream including N-butyraldehyde from the purge gas reactor and combining the second product stream including N-butyraldehyde and the first product stream including N-butyraldehyde; and withdrawing a stream including N-butyraldehyde from the purge gas reactor and recovering N-butyraldehyde from the stream including N-butyraldehyde using a vent condenser.

The above described and other features are exemplified by the following figures and detailed description.

BRIEF DESCRIPTION OF THE DRAWINGS

The following is a brief description of the drawings wherein like elements are numbered alike and which are presented for the purposes of illustrating the exemplary embodiments disclosed herein and not for the purposes of limiting the same.

DETAILED DESCRIPTION

Figure 1:
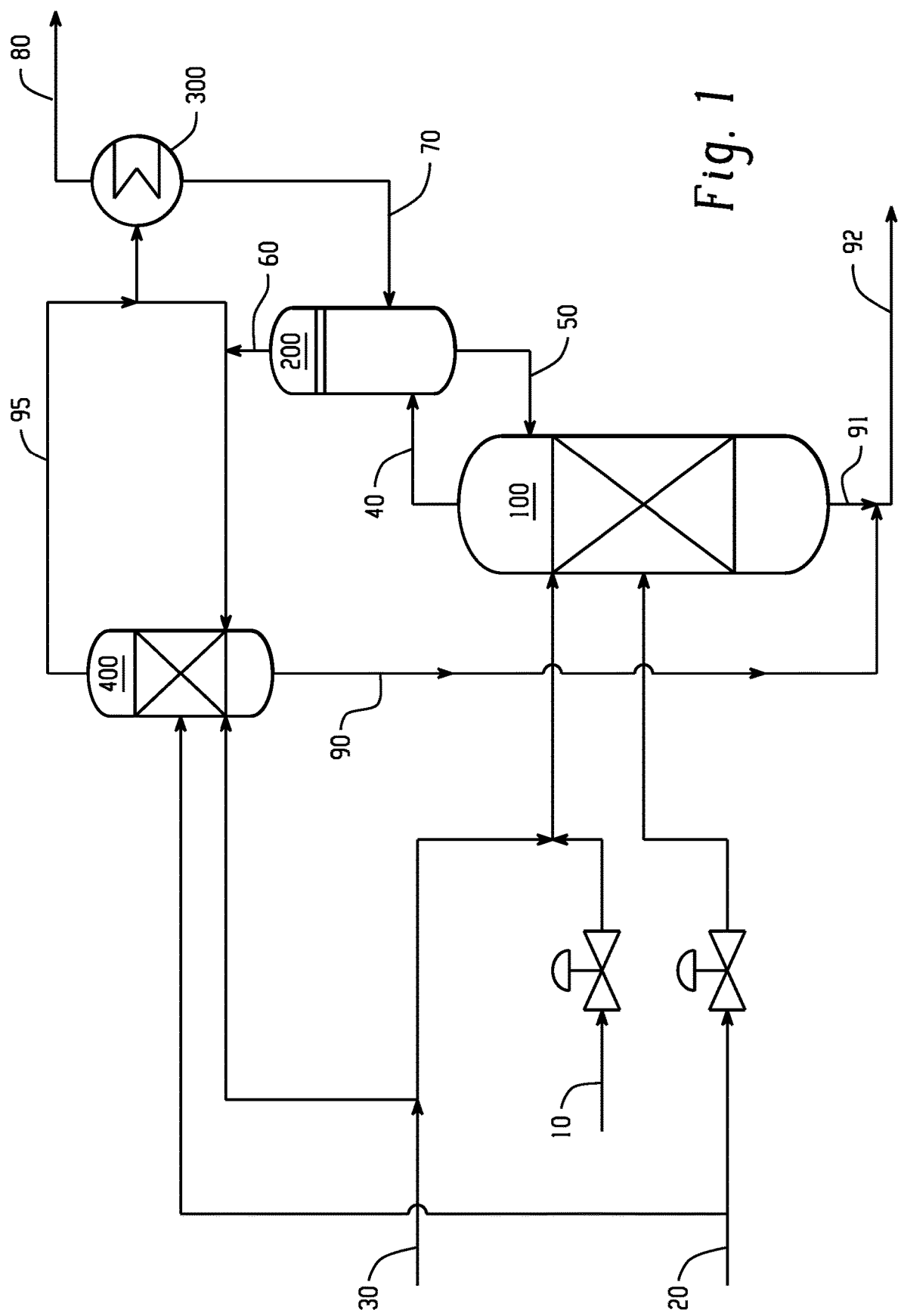
FIG. 1 shows an embodiment of an OXO process.

Disclosed herein are processes of recovering propylene and N-butyraldehyde from a purge gas. An additional reactor is used in series with the other reactors in an OXO process reactor system. The additional reactor can assist in converting propylene in the purge gas to N-butyraldehyde in the presence of syngas and a catalyst. Additionally, the process disclosed herein can allow for N-butyraldehyde in the purge gas to be recovered. For example, greater than or equal to 30%, for example, greater than or equal to 40%, for example, greater than or equal to 50%, for example, greater than or equal to 60% recovery of propylene and N-butyraldehyde can be achieved with the processes disclosed herein. Such increases in recovery can lead to increases in the overall propylene efficiency of the reactor system.

The process disclosed herein can include recovering propylene and N-butyraldehyde from a purge gas. In the process, a first product stream comprising N-butyraldehyde can be formed by reacting propylene and a first synthesis gas in the presence of a first catalyst in a first reactor and a second reactor. A mixed stream comprising N-butyraldehyde and unreacted propylene from the second reactor can be withdrawn at which point a liquid stream and purge gas comprising N-butyraldehyde and unreacted propylene from the mixed stream can be separated and the liquid stream recycled to the second reactor. The purge gas and a second synthesis gas can be reacted in the presence of a second catalyst in a purge gas reactor to form a second product stream comprising N-butyraldehyde. The second product stream comprising N-butyraldehyde can be withdrawn from the purge gas reactor and combined with the first product stream comprising N-butyraldehyde. A stream comprising N-butyraldehyde can be withdrawn from the purge gas reactor and N-butyraldehyde can be recovered from the stream comprising N-butyraldehyde product stream using a vent condenser or an evaporative condenser.

In the process, the first catalyst can include a transition metal catalyst. For example, the first catalyst can comprise rhodium acetylacetonato carbonyl triphenylphosphine. The second catalyst can include a transition metal catalyst. For example, the second catalyst can comprise rhodium acetylacetonato carbonyl triphenylphosphine. The first catalyst and the second catalyst can comprise the same material. The first catalyst and the second catalyst can comprise different materials.

The first reactor, the second reactor, and the purge reactor can be operated in series. It was surprisingly discovered that with the process disclosed herein, greater than or equal to 30% of N-butyraldehyde present in the N-butyraldehyde product stream can be recovered from the purge gas reactor, for example, greater than or equal to 40% can be recovered, for example, greater than or equal to 50% can be recovered, for example, greater than or equal to 60% can be recovered. Also surprising with the presently claimed process is the feature that greater than or equal to 30%, for example, greater than or equal to 40%, for example, greater than or equal to 50%, for example, greater than or equal to 60%, of propylene in the purge gas can be converted to N-butyraldehyde in the purge gas reactor.

Operating conditions of the first reactor can include an operating pressure of 1 MegaPascal to 10 MegaPascals and an operating temperature of 40 to 200° C. Operating conditions of the second reactor can include an operating pressure of 1 MegaPascal to 10 MegaPascals and an operating temperature of 40 to 200° C. Operating conditions of the purge gas reactor can include an operating pressure of 1 MegaPascal to 10 MegaPascals and an operating temperature of 40 to 200° C., for example, 1.5 MegaPascals to 1.8 MegaPascals and 70 to 90° C.

A process of recovering propylene and N-butyraldehyde from a purge gas can include forming a first product stream comprising N-butyraldehyde by reacting propylene and a first synthesis gas in the presence of a first catalyst in a first reactor. A mixed stream comprising N-butyraldehyde and unreacted propylene from the first reactor cam then be withdrawn. A liquid stream and purge gas comprising N-butyraldehyde and unreacted propylene from the mixed stream can be separated using an entrainment separator. The liquid stream can be recycled to the first reactor. The purge gas and a second synthesis gas can be reacted in the presence of a second catalyst in a purge gas reactor to form a second product stream comprising N butyraldehyde. The second product stream comprising N-butyraldehyde can be withdrawn from the purge gas reactor and combined with the first product stream comprising N-butyraldehyde. A stream comprising N-butyraldehyde can be withdrawn from the purge gas reactor and N butyraldehyde can be recovered from the stream comprising N-butyraldehyde using a vent condenser.

In the process, the first catalyst can include a transition metal catalyst. For example, the first catalyst can comprise rhodium, for example, rhodium acetylacetonato carbonyl triphenylphosphine. The second catalyst can include a transition metal catalyst. For example, the second catalyst can comprise rhodium, for example, rhodium acetylacetonato carbonyl triphenylphosphine. The first catalyst and the second catalyst can comprise the same material. The first catalyst and the second catalyst can comprise different materials.

The first reactor, the entrainment separator, and the purge reactor can be operated in series. It was surprisingly discovered that with the process disclosed herein, greater than or equal to 30% of N-butyraldehyde present in the N-butyraldehyde product stream can be recovered from the purge gas reactor, for example, greater than or equal to 40% can be recovered, for example, greater than or equal to 50% can be recovered, for example, greater than or equal to 60% can be recovered. Also surprising with the presently claimed process is the feature that greater than or equal to 30%, for example, greater than or equal to 40%, for example, greater than or equal to 50%, for example, greater than or equal to 60%, of propylene in the purge gas can be converted to N-butyraldehyde in the purge gas reactor.

Operating conditions of the first reactor can include an operating pressure of 1 MegaPascal to 10 MegaPascals and an operating temperature of 40 to 200° C. Operating conditions of the purge gas reactor can include an operating pressure of 1 MegaPascal to 10 MegaPascals and an operating temperature of 40 to 200° C.

A vent condenser can condense condensable components, for example, N-butyraldehyde and Iso-butyraldehyde, and transfer thermal energy to an incoming liquid phase refrigerant, which can transfer the thermal energy to a cooling water system. Generally, entrainment separators can eliminate any mist in the reactor to avoid contamination of the steam or vapor. Entrainment generally refers to the entrapment of one substance by another substance.

A more complete understanding of the components, processes, and apparatuses disclosed herein can be obtained by reference to the accompanying drawings. These figures (also referred to herein as "FIG.") are merely a schematic representation based on convenience and the ease of demonstrating the present disclosure, and are, therefore, not intended to indicate relative size and dimensions of the devices or components thereof and/or to define or limit the scope of the exemplary embodiments. Although specific terms are used in the following description for the sake of clarity, these terms are intended to refer only to the particular structure of the embodiments selected for illustration in the drawing, and are not intended to define or limit the scope of the disclosure. In the drawing and the following description below, it is to be understood that like numeric designations refer to components of like function.

With reference to FIG. 1, in an OXO process, propylene 10 and synthesis gas 20 are reacted in the presence of a first catalyst 30 in an OXO process reactor system 100. The first catalyst 30 can include a transition metal catalyst, for example, rhodium, for example, acetylacetonato carbonyl triphenylphosphine.

A mixed stream including N-butyraldehyde and unreacted propylene, e.g., an overhead product steam, 40 from the OXO process reactor system 100 can be separated into a liquid stream 50 and purge gas including N-butyraldehyde and unreacted propylene 60 in a second reactor 200, e.g., an entrainment separator 200. The liquid stream 50, which can contain catalyst, can be recycled to the reactor system 100. At least a portion of the purge gas 60 can be sent through a vent condenser 300. A stream including N-butyraldehyde 70 that can be recycled to the entrainment separator 200 or sent to a flash condensate drum (not shown) can be recovered from the vent condenser 300. A stream 80 than can be sent to a flare and be used as a fuel gas can also be recovered from the vent condenser 300.

In an embodiment, the reactor system can include a first reactor and a second reactor. The first reactor and the second reactor can be operated in series. The reaction can be initiated in the first reactor and completed in the second reactor. An overhead product steam from the second reactor can be separated into a liquid stream and purge gas in an entrainment separator. The liquid stream, which can contain catalyst, can be sent to the second reactor.

Figure 2:
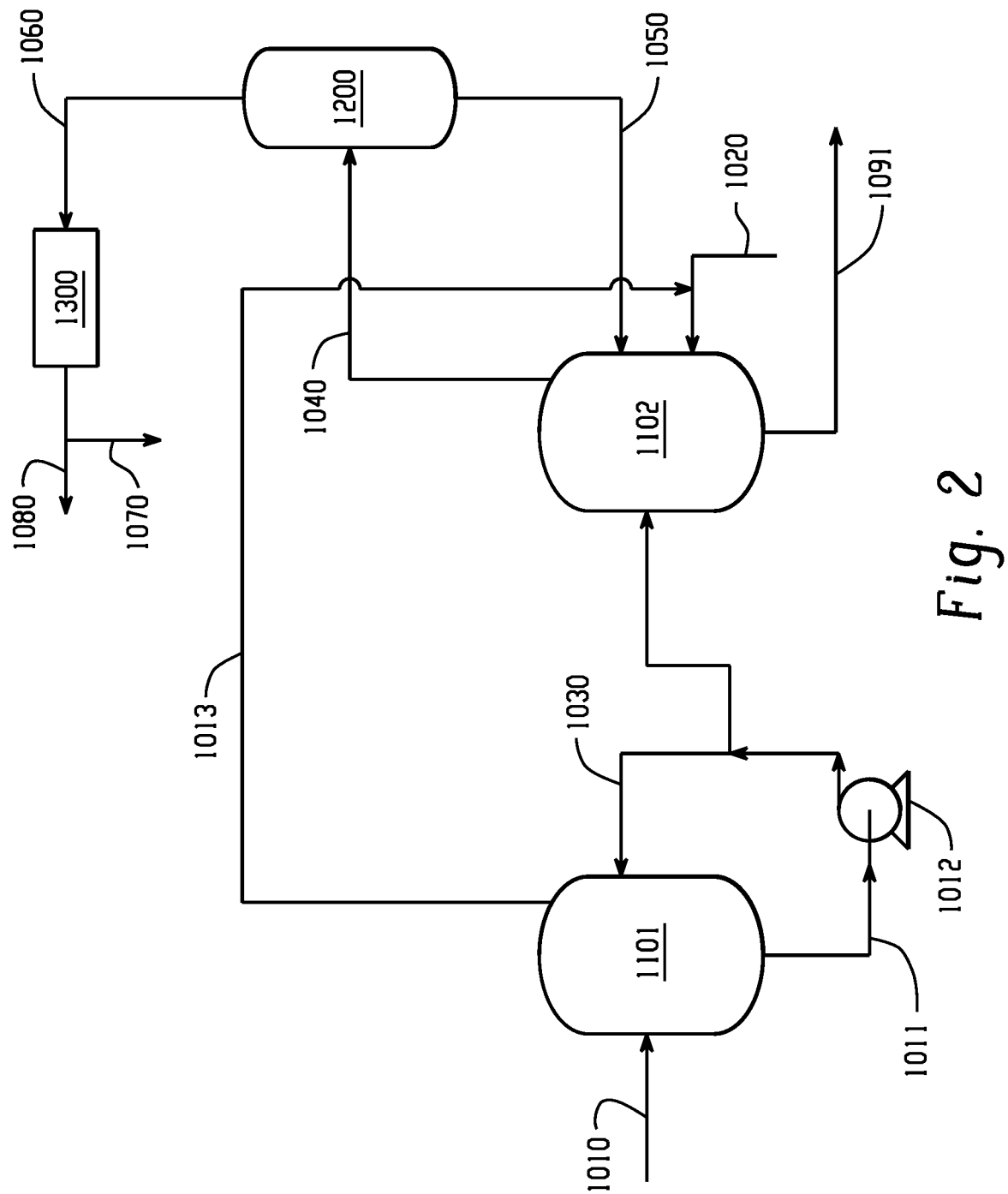
FIG. 2 shows an embodiment of an OXO process including two reactors.

With reference to FIG. 2, propylene 1010 and synthesis gas (feed not shown) are reacted in the presence of a first catalyst 1030 in a first OXO process reactor 1101. The first catalyst 1030 can include a transition metal catalyst, for example, rhodium, for example, acetylacetonato carbonyl triphenylphosphine.

A bottoms product stream 1011 (including propylene and the first catalyst) from the first OXO process reactor 1101 can be fed via pump 1012 to a second OXO process reactor 1102. An overhead product steam 1013 from the first OXO process reactor 1101 can be mixed with synthesis gas 1020, to be fed to second OXO process reactor 1102.

A mixed stream including N-butyraldehyde and unreacted propylene, e.g., an overhead product steam, 1040 from the second OXO process reactor 1102 can be separated into a liquid stream 1050 and purge gas including N-butyraldehyde and unreacted propylene 1060 in a second reactor 1200, e.g., an entrainment separator 1200. The liquid stream 1050, which can contain catalyst, can be recycled to the second OXO process reactor 1102. At least a portion of the purge gas 1060 can be sent through a vent condenser 1300. A stream including N-butyraldehyde 1070 that can be recycled to the entrainment separator 1200 (recycle not shown) or sent to a flash condensate drum (not shown) can be recovered from the vent condenser 1300. A stream 1080 than can be sent to a flare and be used as a fuel gas can also be recovered from the vent condenser 1300.

A product stream including N-butyraldehyde, Iso-butyraldehyde, and the first catalyst 1030, e.g., a bottoms product stream, 1091 can be withdrawn from the second OXO process reactor 1102. The first catalyst 1030 can include catalyst separated from the bottoms product stream 1091 from the second OXO process reactor 1102 (not shown).

The purge gas 60 is fed to a purge gas reactor 400. Propylene in the purge gas 60 can be converted to N-butyraldehyde in the presence of synthesis gas and a second catalyst in the purge gas reactor 400. The purge gas reactor 400 can be operated in series with the reactor system 100, for example, the first reactor, the second reactor, and the purge gas reactor can be operated in series. As shown in FIG. 1, the first reactor 100, the entrainment separator 200, and the purge gas reactor 400 can be operated in series. The second catalyst can include a transition metal catalyst, for example, rhodium, for example, rhodium acetylacetonato carbonyl triphenylphosphine. As shown in FIG. 1, the first catalyst and the second catalyst can include the same material. As also shown in FIG. 1, the first synthesis gas and the second synthesis gas can include the same material.

The purge gas reactor can be operated at the same reaction conditions as the reactor system 100, for example, the first and second reactors. For example, an operating pressure of each of the first reactor, the second reactor, and the purge gas reactor can be 1 MegaPascal to 10 MegaPascals and an operating temperature of the first reactor, the second reactor, and the purge gas reactor can be 40 to 200° C.

A product stream including N-butyraldehyde 90 is withdrawn from the purge gas reactor 400 and can be combined with a product stream including N-butyraldehyde, e.g., a bottoms product stream, 91 from the reactor system 100 to form a combined product stream including N-butyraldehyde 92. The product stream including N-butyraldehyde 90 can include N-butyraldehyde in the purge gas 60. An overhead stream 95 from the purge gas reactor 400 can be sent to the vent condenser 300, optionally with a portion of the purge gas 60.

The purge gas reactor can reduce N-butyraldehyde and propylene losses in the purge gas. Propylene and N-butyraldehyde losses affect the propylene consumption of the overall process. The purge gas reactor can improve, e.g., decrease, propylene consumption and improve overall efficiency of the OXO process. For example, greater than or equal to 30% of N-butyraldehyde present in the N-butyraldehyde product stream can be recovered from the purge gas reactor, for example, greater than or equal to 40% is recovered, for example, greater than or equal to 50% can be recovered, even for example, greater than or equal to 60% can be recovered. Greater than or equal to 30%, for example, greater than or equal to 40%, for example, greater than or equal to 50%, for example, greater than or equal to 60%, of propylene in the purge gas can be converted to N-butyraldehyde in the purge gas reactor.

This disclosure is further illustrated by the following examples, which are non-limiting.

EXAMPLES

Table 1 provides the composition of purge gas according to examples not including a purge gas reactor. The quantity of NBAL in the purge gas was higher than expected (i.e., 5.77-8.02 mol % versus 1.50-2.50 mol %) for an OXO process, and the quantity of propylene in the purge gas was also higher than expected (i.e., 21.01-26.02 mol % versus 10.00-14.00 mol %) for an OXO process.

TABLE 1

|  | $CO_2$ (% mol) | CO (% mol) | $H_2$ (% mol) | IBAL (% mol) | $CH_4$ (% mol) | NBAL (% mol) | $N_2$ (% mol) | Propane (% mol) | Propylene (% mol) |
|---|---|---|---|---|---|---|---|---|---|
| Expected Minimum | 4.00 | 3.00 | 10.00 | 0.20 | 32.00 | 1.50 | 8.00 | 20.00 | 10.00 |
| Expected Maximum | 5.00 | 4.00 | 14.00 | 0.40 | 38.00 | 2.50 | 10.0 | 24.00 | 14.00 |
| Example 1 | 2.99 | 0.67 | 8.76 | 0.88 | 8.12 | 6.14 | 24.66 | 21.76 | 26.02 |
| Example 2 | 2.48 | 0.59 | 7.34 | 0.76 | 7.96 | 5.77 | 23.96 | 25.15 | 25.99 |
| Example 3 | 3.82 | 0.52 | 7.1 | 0.89 | 7.83 | 8.02 | 23.3 | 27.51 | 21.01 |

Calculations for increased NBAL production are carried out on the basis of a purge gas flow rate of 1,200 kilograms per hour (kg/hr), 60% efficiency of propylene conversion in the purge gas reactor (for example, due to the amount of inerts in the purge gas), and 24.34 mol % in the purge gas (i.e., average of Examples 1-3). NBAL recovery from the purge gas is 95%. A benefit of 266 kg/hr propylene conversion and 207.14 kg/hr of NBAL recovery is achieved using a purge gas reactor after the entrainment separator as shown in Table 2.

TABLE 2

| | |
|---|---|
| Purge Gas Flow Rate | 1,200 kg/hr |
| Purge Gas Molecular Weight | 27.71 |
| Propylene Content of the Purge Gas | 24.34 mol % |
| Propylene Flow in the Purge Gas | 442.71 kg/hr |
| Propylene Conversion with 60% Efficiency | 266 kg/hr |
| NBal Flow in the Purge Gas | 207.14 kg/hr |
| NBal Recovery with 60% Efficiency | 124.28 kg/hr |
| 95% Recovered NBal eq. EH | 106.59 kg/hr |

This disclosure further encompasses the following aspects.

Aspect 1. A process of recovering propylene and N-butyraldehyde from a purge gas, comprising: forming a first product stream comprising N-butyraldehyde by reacting propylene and a first synthesis gas in the presence of a first catalyst in a first reactor and a second reactor; withdrawing a mixed stream comprising N-butyraldehyde and unreacted propylene from the second reactor; separating a liquid stream and purge gas comprising N-butyraldehyde and unreacted propylene from the mixed stream and recycling the liquid stream to the second reactor; reacting the purge gas and a second synthesis gas in the presence of a second catalyst in a purge gas reactor to form a second product stream comprising N-butyraldehyde; withdrawing the second product stream comprising N-butyraldehyde from the purge gas reactor and combining the second product stream comprising N-butyraldehyde and the first product stream comprising N-butyraldehyde; and withdrawing a stream comprising N-butyraldehyde from the purge gas reactor and recovering N-butyraldehyde from the stream comprising N-butyraldehyde product stream using a vent condenser.

Aspect 2. The process of Aspect 1, wherein the first catalyst and/or the second catalyst comprises a transition metal catalyst, preferably wherein the catalyst comprises rhodium, more preferably, wherein the first catalyst and/or the second catalyst comprises acetylacetonato carbonyl triphenylphosphine.

Aspect 3. The process of Aspect 1 or Aspect 2, wherein the first reactor, the second reactor, and the purge gas reactor are operated in series.

Aspect 4. The process of any of the preceding aspects, wherein greater than or equal to 30% of N-butyraldehyde present in the N-butyraldehyde product stream is recovered from the purge gas reactor, preferably, wherein greater than or equal to 40% is recovered, more preferably, wherein greater than or equal to 50% is recovered, even more preferably, wherein greater than or equal to 60% is recovered.

Aspect 5. The process of any of the preceding aspects, wherein the first catalyst and the second catalyst comprise the same material.

Aspect 6. The process of any of Aspects 1-4, wherein the first catalyst and the second catalyst comprise different materials.

Aspect 7. The process of any of the preceding aspects, wherein an operating pressure of the first reactor is 1 MegaPascal to 10 MegaPascals and an operating temperature of the first reactor is 40 to 200° C.

Aspect 8. The process of any of the preceding aspects, wherein an operating pressure of the second reactor is 1 MegaPascal to 10 MegaPascals and an operating temperature of the second reactor is 40 to 200° C.

Aspect 9. The process of any of the preceding aspects, wherein an operating pressure of the purge gas reactor is 1 MegaPascal to 10 MegaPascals and an operating temperature of the purge gas reactor is 40 to 200° C.

Aspect 10. The process of any of the preceding aspects, wherein greater than or equal to 30%, preferably, greater than or equal to 40%, more preferably, greater than or equal to 50%, even more preferably, greater than or equal to 60%, of propylene in the purge gas is converted to N-butyraldehyde in the purge gas reactor.

Aspect 11. A process of recovering propylene and N-butyraldehyde from a purge gas, comprising: forming a first product stream comprising N-butyraldehyde by reacting propylene and a first synthesis gas in the presence of a first catalyst comprising rhodium in a first reactor; withdrawing a mixed stream comprising N-butyraldehyde and unreacted propylene from the first reactor; separating a liquid stream and purge gas comprising N-butyraldehyde and unreacted propylene from the mixed stream using an entrainment separator and recycling the liquid stream to the first reactor; reacting the purge gas and a second synthesis gas in the presence of a second catalyst comprising rhodium in a purge gas reactor to form a second product stream comprising N-butyraldehyde; withdrawing the second product stream comprising N-butyraldehyde from the purge gas reactor and combining the second product stream comprising N-butyraldehyde and the first product stream comprising N-butyraldehyde; and withdrawing a stream comprising N-butyraldehyde from the purge gas reactor and recovering N-butyraldehyde from the stream comprising N-butyraldehyde using a vent condenser.

Aspect 12. The process of Aspect 11, wherein the first catalyst and/or the second catalyst comprises rhodium acetylacetonato carbonyl triphenylphosphine.

Aspect 13. The process of Aspect 11 or Aspect 12, wherein the first reactor, the entrainment separator, and the purge gas reactor are operated in series.

Aspect 14. The process of any of Aspects 11-13, wherein an operating pressure of the first reactor is 1 MegaPascal to 10 MegaPascals and an operating temperature of the first reactor is 40 to 200° C.

Aspect 15. The process of any of Aspects 11-14, wherein an operating pressure of the purge gas reactor is 1 MegaPascal to 10 MegaPascals and an operating temperature of the purge gas reactor is 40 to 200° C.

The compositions, methods, and articles can alternatively comprise, consist of, or consist essentially of, any appropriate materials, steps, or components herein disclosed. The compositions, methods, and articles can additionally, or alternatively, be formulated so as to be devoid, or substantially free, of any materials (or species), steps, or components, that are otherwise not necessary to the achievement of the function or objectives of the compositions, methods, and articles.

All ranges disclosed herein are inclusive of the endpoints, and the endpoints are independently combinable with each other (e.g., ranges of "up to 25 wt. %, or, more specifically, 5 wt. % to 20 wt. %", is inclusive of the endpoints and all intermediate values of the ranges of "5 wt. % to 25 wt. %," etc.). "The terms "first," "second," and the like, do not denote any order, quantity, or importance, but rather are used to distinguish one element from another. The terms "a" and "an" and "the" do not denote a limitation of quantity, and are to be construed to cover both the singular and the plural, unless otherwise indicated herein or clearly contradicted by context. "Or" means "and/or" unless clearly stated otherwise. Reference throughout the specification to "an embodiment" means that a particular element described in connection with the embodiment is included in at least one embodiment described herein, and may or may not be present in other embodiments. In addition, it is to be understood that the described elements may be combined in any suitable manner in the various embodiments.

Unless defined otherwise, technical and scientific terms used herein have the same meaning as is commonly understood by one of skill in the art to which this application belongs. All cited patents, patent applications, and other references are incorporated herein by reference in their entirety. However, if a term in the present application contradicts or conflicts with a term in the incorporated reference, the term from the present application takes precedence over the conflicting term from the incorporated reference.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

What is claimed is:

1. A process of recovering propylene and N-butyraldehyde from a purge gas, comprising:
    forming a first product stream comprising N-butyraldehyde by reacting propylene and a first synthesis gas in the presence of a first catalyst in a first reactor and a second reactor;
    withdrawing a mixed stream comprising N-butyraldehyde and unreacted propylene from the second reactor;
    separating a liquid stream and purge gas comprising N-butyraldehyde and unreacted propylene from the mixed stream and recycling the liquid stream to the second reactor;
    reacting the purge gas and a second synthesis gas in the presence of a second catalyst in a purge gas reactor to form a second product stream comprising N-butyraldehyde;
    withdrawing the second product stream comprising N-butyraldehyde from the purge gas reactor and combining the second product stream comprising N-butyraldehyde and the first product stream comprising N-butyraldehyde; and
    withdrawing a stream comprising N-butyraldehyde from the purge gas reactor and recovering N-butyraldehyde from the stream comprising N-butyraldehyde product stream using a vent condenser.

2. The process of claim 1, wherein the first catalyst and/or the second catalyst comprises a transition metal catalyst.

3. The process of claim 1, wherein the first reactor, the second reactor, and the purge gas reactor are operated in series.

4. The process of claim 1, wherein greater than or equal to 30% of N-butyraldehyde present in the N-butyraldehyde product stream is recovered from the purge gas reactor.

5. The process of claim 1, wherein the first catalyst and the second catalyst comprise the same material.

6. The process of claim 1, wherein the first catalyst and the second catalyst comprise different materials.

7. The process of claim 1, wherein an operating pressure of the first reactor is 1 MegaPascal to 10 MegaPascals and an operating temperature of the first reactor is 40 to 200° C.

8. The process of claim 1, wherein an operating pressure of the second reactor is 1 MegaPascal to 10 MegaPascals and an operating temperature of the second reactor is 40 to 200° C.

9. The process of claim 1, wherein an operating pressure of the purge gas reactor is 1 MegaPascal to 10 MegaPascals and an operating temperature of purge gas third reactor is 40 to 200° C.

10. The process of claim 1, wherein greater than or equal to 30% of propylene in the purge gas is converted to N-butyraldehyde in the purge gas reactor.

11. A process of recovering propylene and N-butyraldehyde from a purge gas, comprising:
    forming a first product stream comprising N-butyraldehyde by reacting propylene and a first synthesis gas in the presence of a first catalyst comprising rhodium in a first reactor;
    withdrawing a mixed stream comprising N-butyraldehyde and unreacted propylene from the first reactor;
    separating a liquid stream and purge gas comprising N-butyraldehyde and unreacted propylene from the mixed stream using an entrainment separator and recycling the liquid stream to the first reactor;
    reacting the purge gas and a second synthesis gas in the presence of a second catalyst comprising rhodium in a purge gas reactor to form a second product stream comprising N-butyraldehyde;
    withdrawing the second product stream comprising N-butyraldehyde from the purge gas reactor and combining the second product stream comprising N-butyraldehyde and the first product stream comprising N-butyraldehyde; and
    withdrawing a stream comprising N-butyraldehyde from the purge gas reactor and recovering N-butyraldehyde from the stream comprising N-butyraldehyde using a vent condenser.

12. The process of claim 11, wherein the first catalyst and/or the second catalyst comprises rhodium acetylacetonato carbonyl triphenylphosphine.

13. The process of claim 11, wherein the first reactor, the entrainment separator, and the purge gas reactor are operated in series.

14. The process of claim 11, wherein an operating pressure of the first reactor is 1 MegaPascal to 10 MegaPascals and an operating temperature of the first reactor is 40 to 200° C.

15. The process of claim 11, wherein an operating pressure of the purge gas reactor is 1 MegaPascal to 10 MegaPascals and an operating temperature of the purge gas reactor is 40 to 200° C.

16. The process of claim 1, wherein the first catalyst and/or the second catalyst comprises rhodium.

17. The process of claim 1, wherein the first catalyst and/or the second catalyst comprises acetylacetonato carbonyl triphenylphosphine.

18. The process of claim 1, wherein greater than or equal to 40% of propylene in the purge gas is converted to N-butyraldehyde in the purge gas reactor.

19. The process of claim 1, wherein greater than or equal to 50% of propylene in the purge gas is converted to N-butyraldehyde in the purge gas reactor.

20. The process of claim 1, wherein greater than or equal to 60% of propylene in the purge gas is converted to N-butyraldehyde in the purge gas reactor.

* * * * *